US010996112B2

(12) United States Patent
Levi et al.

(10) Patent No.: US 10,996,112 B2
(45) Date of Patent: May 4, 2021

(54) SYSTEMS AND METHODS FOR CORRECTING LAG BETWEEN SENSOR TEMPERATURE AND AMBIENT GAS TEMPERATURE

(71) Applicant: Maxim Integrated Products, Inc., San Jose, CA (US)

(72) Inventors: Victor Levi, Farmers Branch, TX (US); Michael James D'Onofrio, Dallas, TX (US); Raghunath Puttaiah, Plano, TX (US)

(73) Assignee: Maxim Integrated Products, Inc., San Jose, CA (US)

( * ) Notice: Subject to any disclaimer, the term of this patent is extended or adjusted under 35 U.S.C. 154(b) by 264 days.

(21) Appl. No.: 15/779,356

(22) PCT Filed: Nov. 14, 2016

(86) PCT No.: PCT/US2016/061884
§ 371 (c)(1),
(2) Date: May 28, 2018

(87) PCT Pub. No.: WO2017/095619
PCT Pub. Date: Jun. 8, 2017

(65) Prior Publication Data
US 2019/0078939 A1 Mar. 14, 2019

Related U.S. Application Data

(60) Provisional application No. 62/261,783, filed on Dec. 1, 2015, provisional application No. 62/261,782, filed on Dec. 1, 2015.

(51) Int. Cl.
*G01K 1/02* (2021.01)
*G01K 1/12* (2006.01)
(Continued)

(52) U.S. Cl.
CPC ............ *G01K 1/022* (2013.01); *A61L 2/28* (2013.01); *G01K 1/12* (2013.01); *G01K 7/42* (2013.01);
(Continued)

(58) Field of Classification Search
CPC ............ G01K 1/022; G01K 1/12; G01K 7/42; G01K 13/02; A61L 2/28; G06F 11/3476; G06F 17/40
See application file for complete search history.

(56) References Cited

U.S. PATENT DOCUMENTS 4,429,829 A 2/1984 Dutton
4,687,635 A 8/1987 Kaehler et al.
(Continued)

FOREIGN PATENT DOCUMENTS

KR 101413288 B1 6/2014

OTHER PUBLICATIONS

International Search Report dated Jan. 24, 2017, in International PCT Patent Application No. PCT/US2016/061884, filed Nov. 14, 2016 (2pgs).

(Continued)

*Primary Examiner* — Raymond L Nimox
(74) *Attorney, Agent, or Firm* — North Weber and Baugh LLP; Michael North

(57) ABSTRACT

Various embodiments of the invention provide systems and methods for accurately determining temperatures in harsh environments such as, for example, in a steam autoclave chamber during a sterilization cycle. In certain embodiments, temperature data accuracy is increased by utilizing an IC-based temperature logging device that monitors and compensates for inherent thermal delays that would otherwise cause a discrepancy between temperature as measured by a temperature sensor and the actual ambient gas tem-
(Continued)

perature. By properly correcting for the thermal delay, the data accuracy of the measured gas temperature is thus greatly enhanced.

20 Claims, 6 Drawing Sheets

(51) Int. Cl.
| | | |
|---|---|---|
| *A61L 2/28* | (2006.01) | |
| *G01K 7/42* | (2006.01) | |
| *G06F 7/42* | (2006.01) | |
| *G06F 11/34* | (2006.01) | |
| *G01K 13/02* | (2021.01) | |
| *G06F 17/40* | (2006.01) | |
| *G01K 1/022* | (2021.01) | |

(52) U.S. Cl.
CPC .......... *G01K 13/02* (2013.01); *G06F 11/3476* (2013.01); *G06F 17/40* (2013.01)

(56) References Cited

U.S. PATENT DOCUMENTS

| | | | | |
|---|---|---|---|---|
| 5,422,276 | A * | 6/1995 | Colvin | A61L 2/28 422/109 |
| 2011/0198255 | A1* | 8/2011 | Baumfalk | A61J 1/10 206/459.1 |
| 2015/0374868 | A1* | 12/2015 | Bruce | A61L 2/07 422/3 |
| 2016/0004956 | A1* | 1/2016 | Reynolds | A61L 2/07 377/15 |
| 2016/0048752 | A1* | 2/2016 | Reynolds, IV | A61L 2/00 377/15 |

OTHER PUBLICATIONS

Written Opinion dated Jan. 24, 2017, in International PCT Patent Application No. PCT/US2016/061884, filed Nov. 14, 2016 (7pgs).

* cited by examiner

SYSTEMS AND METHODS FOR CORRECTING LAG BETWEEN SENSOR TEMPERATURE AND AMBIENT GAS TEMPERATURE

CROSS REFERENCE TO RELATED PATENT APPLICATIONS

This is a U.S. 371 National Stage of PCT Patent Application No. PCT/US2016/61884, entitled, "SYSTEMS AND METHODS FOR CORRECTING LAG BETWEEN SENSOR TEMPERATURE AND AMBIENT GAS TEMPERATURE," naming as inventors Victor Levi, Michael James D'Onofrio, and Raghunath Puttaiah, and filed Nov. 14, 2016, which application claims priority benefit, under 35 U.S.C. § 119(e), to co-pending and commonly assigned U.S. Provisional Patent Application No. 62/261,783, entitled "ALGORITHM TO CORRECT LAG BETWEEN INTERNAL TEMPERATURE SENSOR AND AMBIENT GAS," naming as inventors Victor Levi, Michael James D'Onofrio, and Raghunath Puttaiah, U.S. Provisional Patent Application No. 62/261,749, entitled, "APPARATUS FOR LOGGING DATA IN HARSH ENVIRONMENTS," naming as inventors Jeffery Alan Gordon, Scott Edward Jones, and Hal Kurkowski, and U.S. Provisional Patent Application No. 62/261,782, entitled, "INDICATOR OF STERILIZATION EFFICACY USING A DATA LOGGER WITH CLOUD/SOFTWARE APPLICATION," naming as inventors Michael James D'Onofrio, Carlos Manuel Contreras, and Raghunath Puttaiah, which applications were filed Dec. 1, 2015, and which applications are hereby incorporated herein by reference in their entireties.

BACKGROUND

A. Technical Field

The present invention relates to data processing, and more particularly, to systems and methods for correcting lag between internal temperature sensor and ambient gas.

B. Background of the Invention

Over the years, various devices for acquiring and storing temperature data have been developed to trace the history of ambient temperature surrounding the devices. Manufacturers and/or distributors send the device along with their products, such as drugs, that are sensitive to temperature changes, where the products need to remain within a preset temperature range to keep their original efficacy. The receivers of the products retrieve the temperature data stored in the device and check if the temperature of the products was outside the preset range during transportation.

Some conventional devices for logging temperature data have been designed to operate at relatively large time constants. For instance, a typical device for monitoring the ocean temperature may have a water-proof capsule and take a sample at every hour. Typically, the capsule is made of thick metal plate, and there is a time lag between the ocean water and the temperature inside the capsule. In such a case, the time constant for the device is in the order of minute, and thus, the time lag due to the large thermal mass of the capsule may not affect the accuracy of the data.

In other applications, such as autoclave for steam sterilization, the time constant is relatively short since the ambient gas temperature inside the autoclave rises from room temperature to 100° C. quite quickly. When a conventional device for logging temperature data is placed inside the autoclave, the device may not be able to keep up with the temperature change due to the thermal resistance of the capsule material. The thermal resistance may result in false reading of the ambient gas temperature. For instance, the conventional device may take longer to heat up relative to the ambient gas in the autoclave than to cool down relative to the ambient gas. As a result, the device may indicate that the autoclave is maintained at the intended sterilization temperature shorter than it actually does. As such, there is a need for a device for electronically logging temperature data, where the time constant of the capsule is short enough to accurately keep track of the ambient gas temperature.

The delay between the ambient gas temperature and the temperature measured by the device may be affected by several factors including the thermal mass of the capsule. If the delay is corrected properly, the accuracy in reading the ambient gas temperature would be enhanced. As such, there is also a need for systems and methods for correcting the delay to thereby accurately track the ambient gas temperature.

BRIEF DESCRIPTION OF THE DRAWINGS

References will be made to embodiments of the invention, examples of which may be illustrated in the accompanying figures. These figures are intended to be illustrative, not limiting. Although the invention is generally described in the context of these embodiments, it should be understood that it is not intended to limit the scope of the invention to these particular embodiments.

DETAILED DESCRIPTION OF THE PREFERRED EMBODIMENTS

In the following description, for the purposes of explanation, specific details are set forth in order to provide an understanding of the invention. It will be apparent, however, to one skilled in the art that the invention can be practiced without these details. One skilled in the art will recognize that embodiments of the present invention, described below, may be performed in a variety of ways and using a variety of means. Those skilled in the art will also recognize additional modifications, applications, and embodiments are within the scope thereof, as are additional fields in which the invention may provide utility. Accordingly, the embodiments described below are illustrative of specific embodiments of the invention and are meant to avoid obscuring the invention.

A reference in the specification to "one embodiment" or "an embodiment" means that a particular feature, structure, characteristic, or function described in connection with the embodiment is included in at least one embodiment of the invention. The appearance of the phrase "in one embodiment," "in an embodiment," or the like in various places in the specification are not necessarily all referring to the same embodiment.

Connections illustrated in the figures between components may be modified or otherwise changed through the addition thereto of intermediary components, without departing from the teachings of the present invention.

Furthermore, one skilled in the art shall recognize: (1) that certain steps may optionally be performed; (2) that steps may not be limited to the specific order set forth herein; and (3) that certain steps may be performed in different orders, including being done contemporaneously.

Figure 1A:
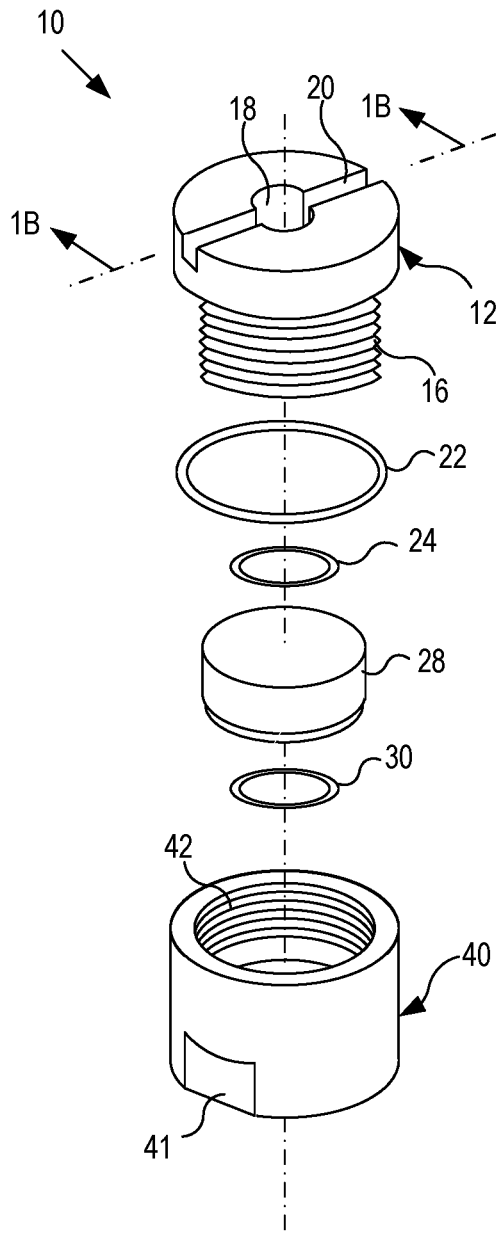
FIGS. 1A-1C show a package for logging temperature data according to one embodiment of the present invention.
Figure 1B:
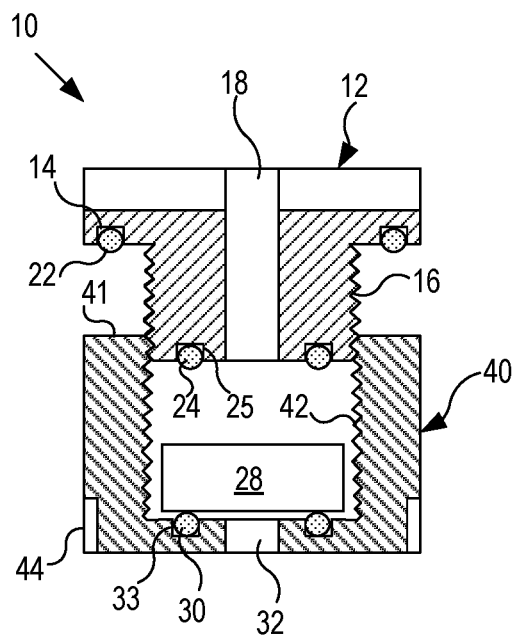
Figure 1C:
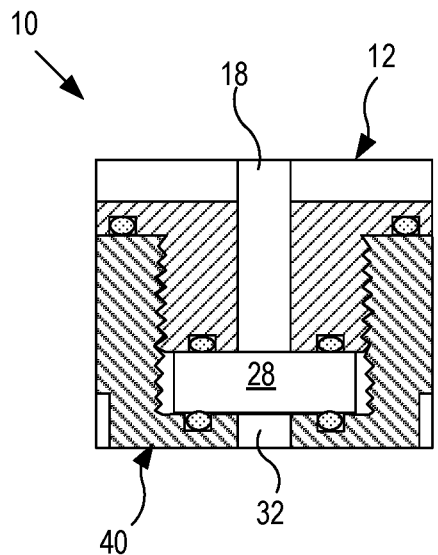

FIG. 1A shows an exploded view of a package 10 for logging temperature data according to one embodiment of the present invention. As depicted in FIG. 1A, the package 10 includes: a capsule having a plug 12, a base 40 and O-rings 22, 24, and 30; and a temperature data logger (or, shortly, data logger) 28 for logging temperature data under harsh environments. In embodiments, the data logger 28 may be an integrated circuit (IC)-based temperature data logger. FIG. 1B shows a cross sectional view of the package 10, taken along the direction 1B-1B, where the male thread 16 of the plug 12 is slightly engaged into the female thread 42 of the base 40. FIG. 1C shows the package 10, where the plug 12 is fully engaged into the base 40.

For the purpose of illustration, the package 10 is described as a temperature data logging device for a steam autoclave chamber, i.e., the package 10 is mounted inside a steam autoclave chamber and logs temperature data during sterilization cycles of the autoclave. For instance, an exemplary operational condition of the steam autoclave has the temperature of 140° C. and the pressure of 2 atmosphere, and each cycle may last 35-40 minutes, and the package 10 is designed to survive more than hundred cycles without being damaged by the ambient gas. However, it should be apparent to those of ordinary skill in the art that the package 10 may be applied to other test environments. Also, it should be apparent to those of ordinary skill in the art that the package 10 may be calibrated to accommodate different operational temperature ranges.

The plug 12 includes: a slot 20 for receiving a tool, such as torque wrench, for turning the plug 12 relative to the base 40; and a through hole 18 that allows the ambient gas to directly contact the top surface of the data logger 28 during operation. Since the ambient gas including hot steam is in direct contact with the data logger 28, the thermal lag between the chamber environment and the data logger 28 is reduced so that the data logger 28 can accurately track the temperature variation inside the chamber.

The O-rings 22, 24, and 30 are used to prevent ingress of moisture into the data logger 28. The O-ring 22 rests on a groove 14 that is formed on the plug 12. The O-ring 22 is compressed by the lip 41 of the base 40 when the plug 12 is fully engaged into the base 40, as shown in FIG. 1C, to thereby preventing ingress of the ambient gas through the gap between the male thread 16 and the female thread 42.

The O-rings 24 and 30 rest on grooves 25 and 33, respectively. When the package 10 is assembled, the O-rings 24 and 30 are compressed by the top and bottom surfaces of the data logger 28, respectively, to thereby prevent ingress of the ambient gas through the gaps between the capsule and the data logger 28.

The base 40 includes a through hole 32 that allows the ambient gas to directly contact the bottom surface of the data logger 28 during operation. Since the ambient gas is in direct contact with the data logger 28, the thermal lag between the chamber environment and the data logger 28 is reduced so that the data logger 28 can accurately track the temperature variation inside the chamber. The base 40 also includes a notch/recess 41 so that a proper device securely holds the base in place during assembly of the package 10.

If the package 10 is assembled while the O-rings 22, 24, and 30 are dry, the O-rings may not properly seal the space surrounding the data logger 28 due to pinching, crimping, or twisting of the O-rings. To avoid such deformation of the O-rings, small amount of grease is applied to the O-rings. The grease also holds the O-rings in their corresponding grooves temporarily during assembly. For instance, the O-rings 22 and 24 remain seated on the grooves 14 and 25, respectively, by the grease when the plug 12 is flipped over during assembly, as shown in FIG. 1B.

It is noted that the package 10 may be mounted in the autoclave chamber with other items, such as medical instruments, being sterilized. If the package 10 releases any toxic material into the autoclave chamber, the items may be contaminated by the toxic material. As such, all of the components, including the grease, of the package 10 are tested to ensure that none of the components release toxins during sterilization cycles.

The capsule is reusable, i.e., the user can disengage the male thread 16 from the female thread 42, replace the data logger 28, and reassemble the package 10. During this process, the user may not place one or more of the O-rings 22, 24 and 30 properly i.e., the user may misalign the O-rings on resealing. In embodiments, to obviate the improper reassembly by the user, small amount of glue may be applied to the threads so that the plug and base are glued together.

Figure 2:
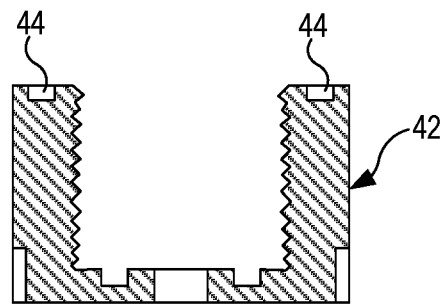
FIG. 2 shows a cross sectional view of a base of a capsule according to one embodiment of the present invention.

FIG. 2 shows a cross sectional view of a base 42 of a capsule according to one embodiment of the present invention. As depicted, the base 42 is similar to the base 40 in FIGS. 1A-1C, with the difference that the base 42 includes an O-ring groove 44 that the O-ring 22 rests on. It should be apparent to those of ordinary skill in the art that the package 10 may include other suitable types of sealing mechanisms to prevent the ingress of the ambient gas into the data logger 28.

The material for the plug 12 and base 40 (or 42) may be chosen for its mechanical properties (i.e., they remain stable during both long and short-term exposure to high temperature and pressure), inherent flame resistance, and outstanding chemical resistance (i.e., inert to high temperature steam, strong bases, fuels and acids). In embodiments, the plug and base are formed of a polymer, such as polyphenylene sulfide (PPS). Likewise, the material for the O-rings 22, 24, and 30 may be chosen for their mechanical strength and chemical qualities. In embodiments, the O-rings are formed of silicon, where the silicon O-rings are also resistant to sunlight, ozone, oxygen, and UV light.

Figure 3:
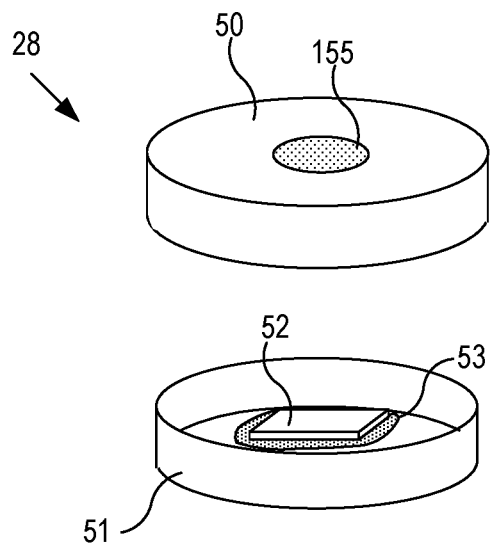
FIG. 3 shows an integrated circuit (IC)-based temperature data logger according to one embodiment of the present invention.

FIG. 3 shows an integrated circuit (IC)-based temperature data logger 28 according to one embodiment of the present invention. As depicted, the temperature logger 28 includes: a top cover 50; a bottom cover 51; an electrical circuitry 52 for measuring and storing the temperature data; and a securing element 53 that secures the electrical circuitry 52 to the bottom cover 51. When the data logger 28 is assembled, the top and bottom covers 50 and 51 form a housing and the electrical circuitry 52 is disposed in the inner space of the housing. In embodiments, the top and bottom covers 50 and 51 may provide water-proof sealing against fluid.

In embodiments, the top and bottom covers 50 and 51 may be formed of electrically conducting material and operate as two electrodes that are electrically connected to the electrical circuitry 52. For instance, a suitable electrical device may communicate the data logged in the data logger 28 through the top and bottom covers 50 and 51. The top and bottom covers 50 and 51 are formed of material having high thermal conductivity, such as metal, so that the lag between the temperature of the autoclave chamber and the temperature inside the covers 50 and 51 is minimized. The securing element 53 is formed of material having a high thermal conductivity, such as heat conducting glue, to minimize the thermal lag between the temperature inside the covers 50 and 51 and the temperature outside the covers.

Unlike the conventional temperature loggers, a portion 155 of the top cover 50 is directly exposed to the ambient gas via the through hole 18 without damaging the electric circuitry 52 during operation. Likewise, a portion of the bottom cover 51 is directly exposed to the ambient gas via the through hole 32 during operation. This feature allows the data logger 28 to have minimal temperature lag, i.e., the data logger 28 can track the ambient gas temperature more accurately.

Figure 4:
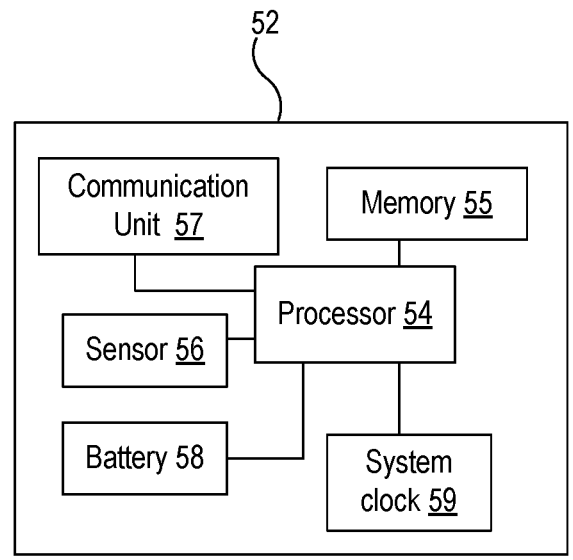
FIG. 4 shows a schematic diagram of an electric circuitry of the IC-based temperature data logger in FIG. 3 according to one embodiment of the present invention.

FIG. 4 shows a schematic diagram of the electronic circuitry 52 of the IC-based temperature data logger 28 in FIG. 3 according to one embodiment of the present invention. In embodiments, the electrical circuitry 52 may be an application-specific integrated circuit (ASIC) and include: a processor 54 for operating various components of the circuitry 52; a sensor 56 for measuring temperature; a battery 58 for providing electrical power to the circuitry 52; a communication unit 57 for communicating data to an external device; a memory 55 for storing the measured temperature data; and a system clock 59 for generating clock signals for the circuitry 52. It is noted that, depending on the application, the circuitry 52 may include additional components, such as additional sensors, and one or more of the components of the circuitry 52 may be omitted.

In embodiments, the processor 54 may be programmed to measure the temperature inside the data logger 28 at a preset time and/or repeat measurements at a preset time interval. In embodiments, the processor 54 may receive the clock signals from the system clock 59 and cause the sensor 56, such as digital temperature sensor, to measure the temperature as scheduled. Then, the processor 54 may store the data into the memory 55, where the memory 55 may be a static RAM, for instance. In embodiments, to minimize the power consumption, the processor 54 may wake up at the scheduled time to measure the temperature and goes back to sleep mode after measurement is completed.

Figure 5:
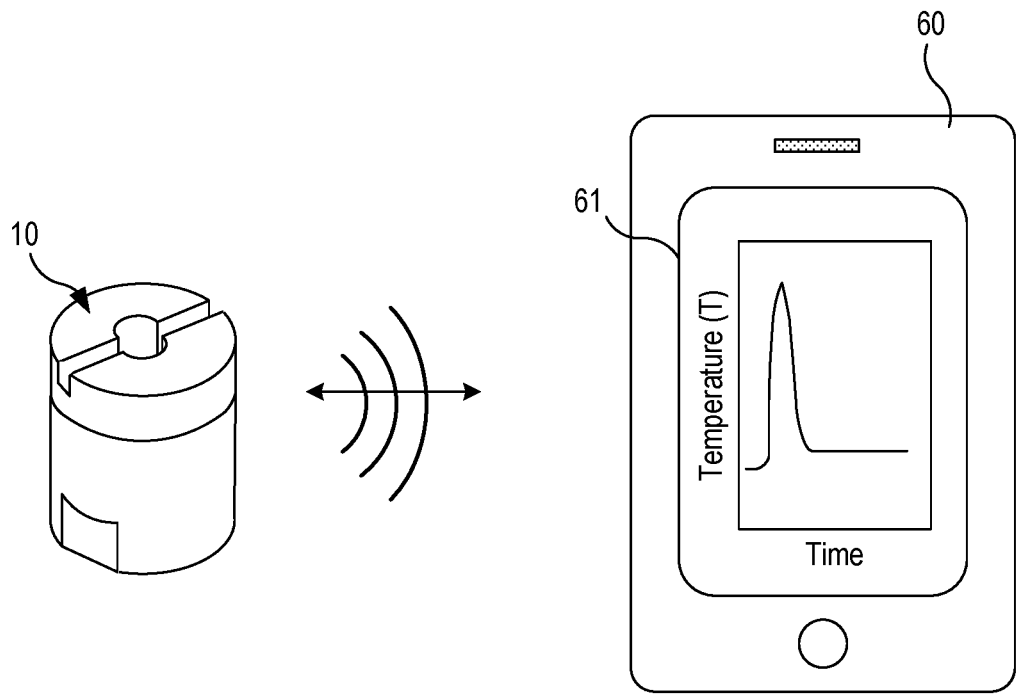
FIG. 5 shows a data communication between the package in FIG. 1A and a mobile device according to one embodiment of the present invention.

In embodiments, the processor 54 may communicate the stored data to an external device through the communication device 57 and/or the processor 54 may be controlled/programmed through the communication device 57. In embodiments, the communication unit 57 may be a wireless communication device. FIG. 5 shows a data communication between the package 10 and a mobile device 60 according to one embodiment of the present invention.

In embodiments, the user may install an application on the mobile device 60 so that the user can set up the parameters on the circuitry 52, such as time and frequency of data sampling, before the package 10 is mounted in the autoclave. After a sterilization cycle(s), the user may retrieve the stored data from the package 10 using the mobile device 60 and a suitable application may display the temperature data on the display 61 of the mobile device 60. It is noted that the user may control and communicate to the package 10 using other suitable external devices. For instance, in embodiments, the user may use a computer/server in place of the mobile device 60.

Figure 6:
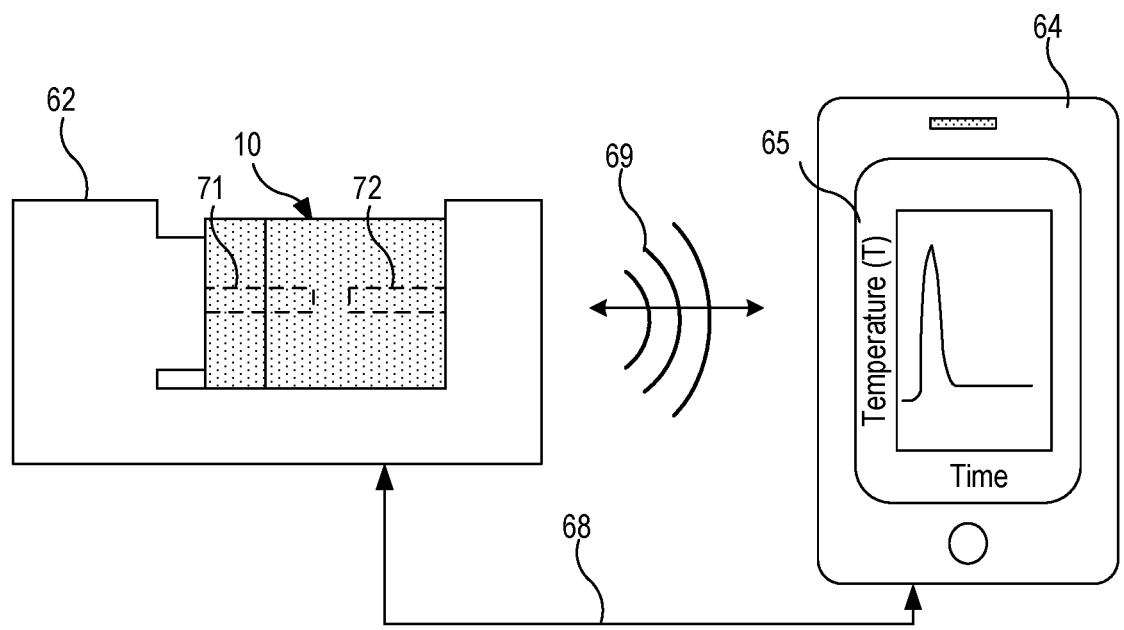
FIG. 6 shows a data communication between the package in FIG. 1A and a mobile device according to one embodiment of the present invention.

FIG. 6 shows a data communication between the package 10 and a mobile device 64 according to one embodiment of the present invention. As depicted, the package 10 may be docked in a reader 62 that can retrieve data stored in the package 10 and send the retrieved data to the mobile device 64. In embodiments, the reader 62 may have two spring-loaded electrodes 71 and 72 that make electrical contact to the top and bottom surfaces of the data logger 28, respectively, and extract the data stored in the package 10. Also, in embodiments, the reader 62 may be used to transmit electrical signals from the mobile device 64 to the package 10 so that the user can program the electrical circuitry 52.

After a sterilization cycle(s), the user may retrieve the stored data from the package 10 using the mobile device 64 and a suitable application installed in the mobile device 64 displays the temperature data on the display 65 of the mobile device 64. It is noted that the user may control and communicate to the package 10 using other suitable external device. For instance, in embodiments, the user may use a computer/server in place of the mobile device 64. In some embodiments, the reader 62 may exchange electrical signals with the mobile device 64 through wireless communication 69, as shown in FIG. 6, or through wire 68, such as universal serial bus (USB) connection.

Figure 7:
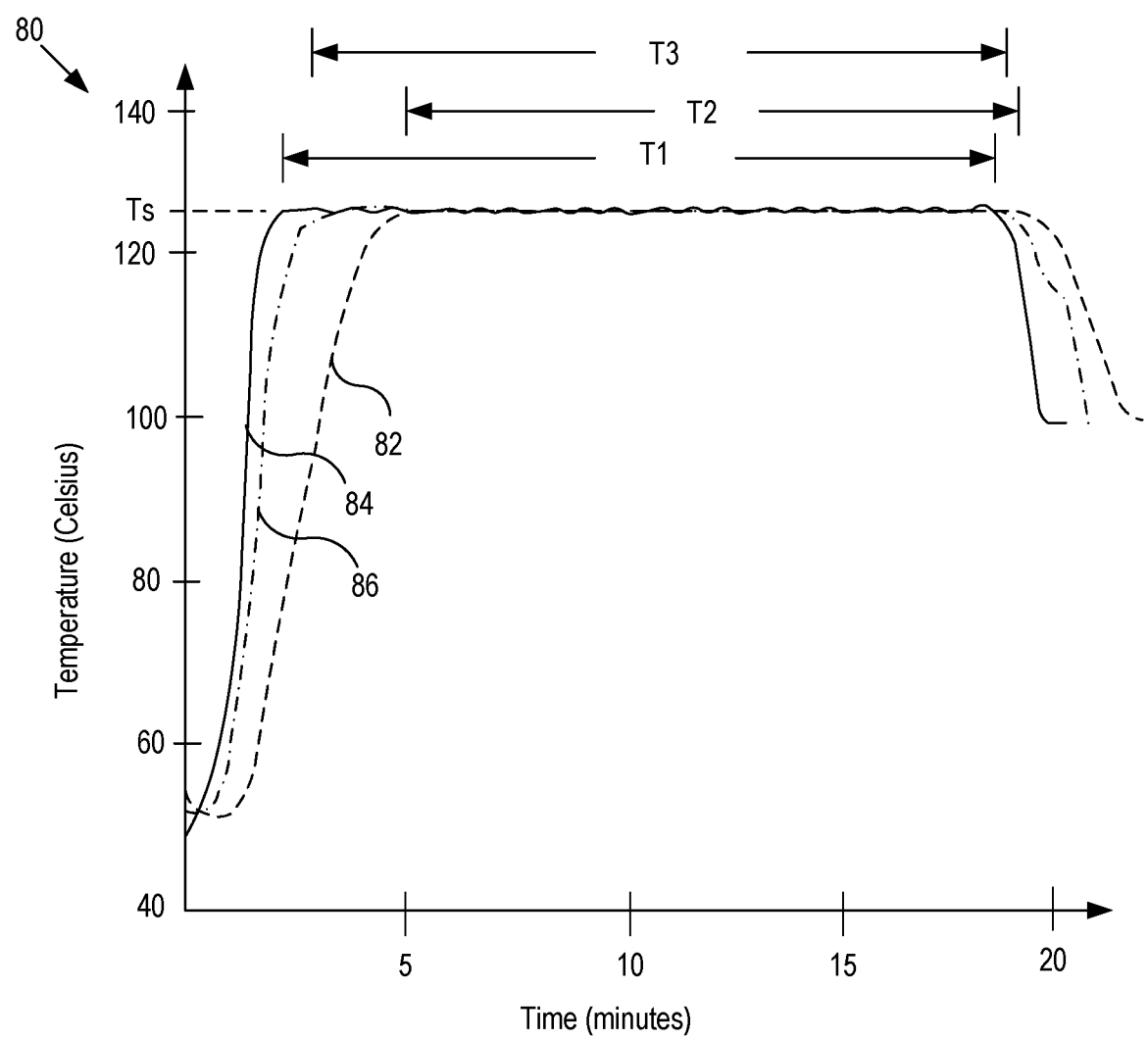
FIG. 7 shows a plot of temperature with and without correction according to one embodiment of the present invention.

FIG. 7 shows an exemplary plot of ambient gas temperature 84 and the temperature 82 measured by the package 10 during a sterilization cycle according to one embodiment of the present invention. As depicted, there is a lag between the ambient gas temperature 84 and the measured temperature 82, i.e., the measured temperature 82 shows that the ambient gas reaches the target sterilization temperature, Ts, several minutes after the ambient gas actually reached Ts. In FIG. 7, T1 represents the time interval during which the ambient gas is actually maintained at Ts while the measured temperature 82 indicates that the ambient gas is maintained at Ts during the time interval T2. For the purpose of illustration, it is assumed that T1 is longer than the required time interval for proper sterilization while T2 is shorter than the required time interval for proper sterilization. If the pass/fail test of the sterilization cycle is determined based on whether the ambient gas is maintained at Ts longer than the required time interval, the measured temperature 82 may indicate that the sterilization cycle failed the test, while the sterilization cycle actually passed the test.

To correct the lag, the mobile device 60, computer/server, or any other computing device may have a software program (or, shortly, algorithm) that analyzes the measured temperature 82. In embodiments, the algorithm may be based on phenomenological model of heat transfer between ambient gas (A) and probe/sensor (P) 56 via the probe enclosure (E), where the enclosure may collectively refer to the plug 12, base 40, and top and bottom covers 50 and 51.

Assuming that the enclosure temperature $T_E$ differs from both actual ambient gas temperature $T_A$ and probe temperature $T_P$, the rate of heat transfer between the probe enclosure and the probe is expressed as:

$$Cp \frac{dTp}{dt} = k_1(T_E - Tp) \qquad (1)$$

where, the parameters $C_P$ and $k_1$ are the heat capacity and heat transfer coefficient of the probe, respectively.

Likewise, the rate of heat transfer between the ambient gas and probe enclosure is expressed as:

$$C_E \frac{dT_E}{dt} = k_2(T_A - T_E) \qquad (2)$$

where, the parameters $C_E$ and $k_2$ are the heat capacity and heat transfer coefficient of the probe enclosure, respectively.

Combining Eq. (1) and Eq. (2), the relation between the ambient gas temperature $T_A$ and the probe temperature $T_P$ is expressed as:

$$T_A = Tp + (\tau_1 + \tau_2)\frac{dTp}{dt} + (\tau_1 \tau_2)\frac{d^2Tp}{dt^2} \qquad (3)$$

where, $\tau_1$ ($=C_p/k_1$) and $\tau_2$ ($=C_E/k_2$) are time constants for the probe and probe enclosure, respectively.

Figure 8:
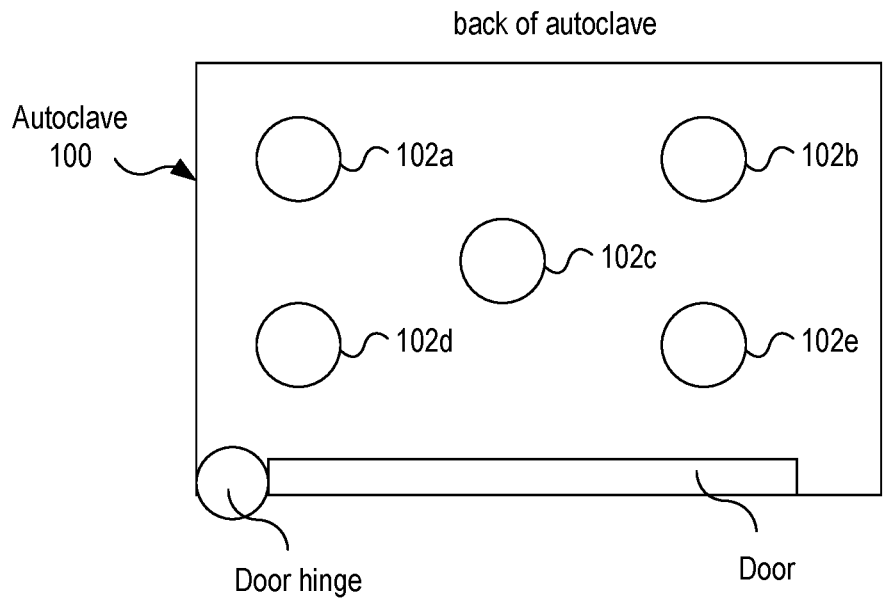
FIG. 8 shows multiple packages inside an autoclave according to one embodiment of the present invention.

In embodiments, several factors may affect the actual values of the time constants, $\tau_1$ and $\tau_2$. FIG. 8 shows multiple devices under test (DUT) 102a-102e located inside an autoclave 100 according to one embodiment of the present invention. In embodiments, each of the DUT 102 may be similar to the package 10. As depicted, depending on the locations where the DUT 102 are installed, the time constants ($\tau_1$ and $\tau_2$) of each device may have different values.

In embodiments, the values of the time constants may vary depending on other parameters: (1) whether the package is bagged or unbagged in a pouch during the sterilization cycle; (2) whether the autoclave is unloaded or loaded with other items, such as medical instruments, during the sterilization cycle; (3) whether the autoclave is already warm before the cycle; (4) the type of cycles, such as vacuum or gravity; (5) the time interval during which the target sterilization temperature Ts is maintained; and (6) the value of Ts. It is noted that other factors may affect the values of the time constants.

In embodiments, the time constants $\tau_1$ and $\tau_2$ in Eq. (3) may be determined, considering the factors described above. For instance, test cycles may be repeated to measure temperature while one or more of the factors are varied. Then, using the obtained temperature data, the time constants may be determined/calibrated.

Eq. (3) includes the first and second derivatives of the probe temperature $T_P$ with respect to time. In embodiments, temperature data may be obtained as an array of samples taken at preset time intervals. Then, the derivatives may be calculated by applying the finite-difference-approximation to the obtained data. In embodiments, a filter, such as low pass filter, may be used to filter the noise in the obtained data before the data is analyzed.

In embodiments, the software application (or algorithm) installed in the mobile device 60 (or, in other suitable external devices) may use Eq. (3) to compensate the lag between the actual ambient gas temperature 84 and measured temperature 82. In FIG. 7, the compensated temperature 86 is obtained by compensating the lag in the measured temperature 82, where the compensated temperature 86 indicates that the ambient gas is maintained at Ts during the time interval T3. If T3 is longer than the required time interval for proper sterilization, the compensated temperature 86 correctly indicates that the sterilization cycle passed the test. Thus, the compensation of the lag reduces the rate of false fails.

Figure 9:
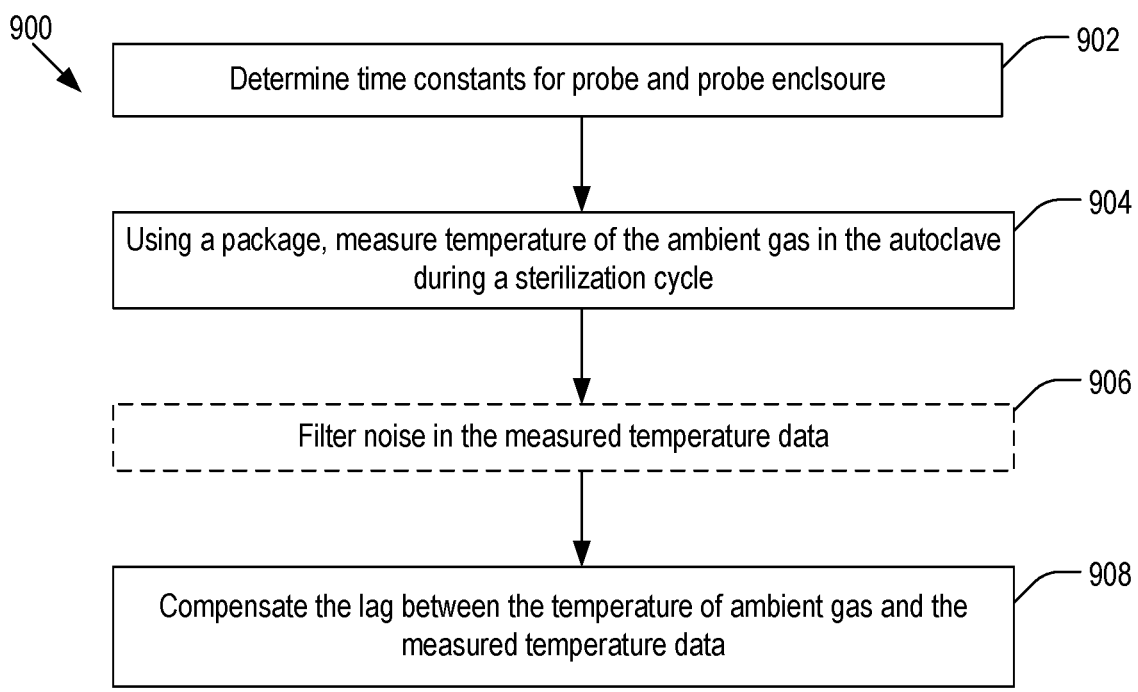
FIG. 9 is a flowchart illustrating exemplary steps that may be carried out to compensate the thermal lag according to one embodiment of the present invention.

FIG. 9 is a flowchart 900 illustrating exemplary steps that may be carried out to compensate the thermal lag according to one embodiment of the present invention. At step 902, the time constants, $\tau_1$ and $\tau_2$ in Eq. (3), are determined. In embodiments, the time constants are determined considering various factors that include (1) the location of the package 10 inside the autoclave; (2) whether the package is bagged or unbagged in a pouch during the sterilization cycle; (3) whether the autoclave is unloaded or loaded with other items, such as dental instruments, during the sterilization cycle; (4) whether the autoclave is already warm before the cycle; (5) the type of cycles, such as vacuum or gravity; (6) the time interval during which the target sterilization temperature Ts is maintained; and (7) the value of Ts. In embodiments, test cycles may be repeated to measure temperature using the package 10 while one or more of the factors are varied. Then, using obtained temperature data, the time constants may be determined.

Next, at step 904, using a package 10, temperature of the ambient gas in the autoclave is measured at a preset time and/or repeat measurements at a preset time interval. Optionally, the noise in the measured temperature data is filtered out by a filter at step 906.

At step 908, the lag between the actual ambient gas temperature and the measured temperature is compensated. In embodiments, Eq. (3) may be applied to the measured temperature data in order to generate compensated temperature data, where the compensated temperature data includes reduce thermal lag and thus more accurately shows the actual ambient gas temperature profile.

In embodiments, one or more computing system may be configured to perform one or more of the methods, functions, and/or operations presented herein. Systems that implement at least one or more of the methods, functions, and/or operations described herein may comprise an application or applications operating on at least one computing system. The computing system may comprise one or more computers and one or more databases. The computer system may be a single system, a distributed system, a cloud-based computer system, or a combination thereof.

It shall be noted that the present disclosure may be implemented in any instruction-execution/computing device or system capable of processing data, including, without limitation phones, laptop computers, desktop computers, and servers. The present disclosure may also be implemented into other computing devices and systems. Furthermore, aspects of the present disclosure may be implemented in a wide variety of ways including software (including firmware), hardware, or combinations thereof. For example, the functions to practice various aspects of the present disclosure may be performed by components that are implemented in a wide variety of ways including discrete logic components, one or more application specific integrated circuits (ASICs), and/or program-controlled processors. It shall be noted that the manner in which these items are implemented is not critical to the present disclosure.

Figure 10:
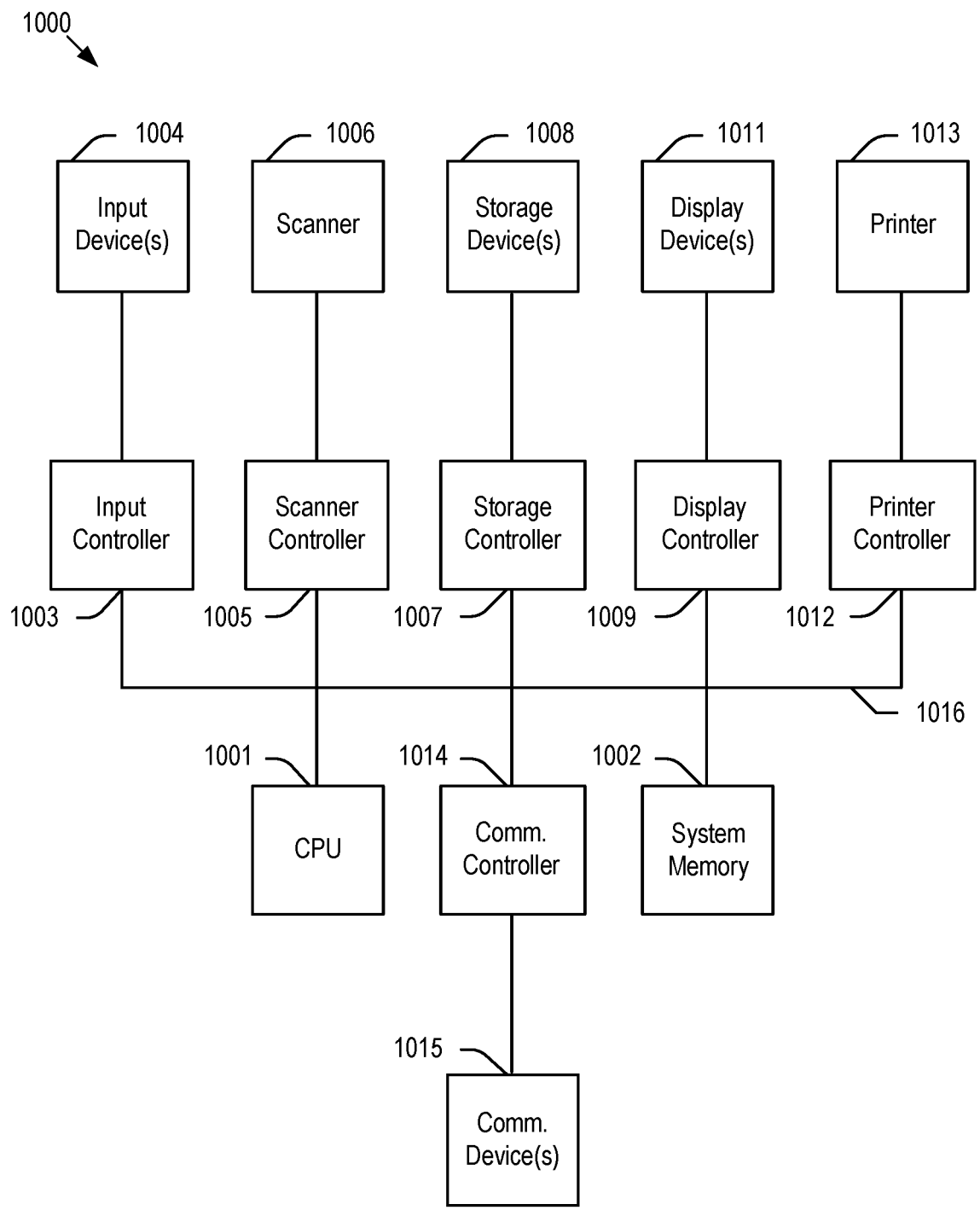
FIG. 10 shows a computer system according to embodiments of the present invention.

Having described the details of the disclosure, an exemplary system 1000, which may be used to implement one or more aspects of the present disclosure, will now be described with reference to FIG. 10. Each client/server in FIG. 1 includes one or more components in the system 1000. As illustrated in FIG. 10, system 1000 includes a central processing unit (CPU) 1001 that provides computing resources and controls the computer. CPU 1001 may be implemented with a microprocessor or the like, and may also include a graphics processor and/or a floating point coprocessor for mathematical computations. System 1000 may also include a system memory 1002, which may be in the form of random-access memory (RAM) and read-only memory (ROM).

A number of controllers and peripheral devices may also be provided, as shown in FIG. 10. An input controller 1003 represents an interface to various input device(s) 1004, such as a keyboard, mouse, or stylus. There may also be a scanner controller 1005, which communicates with a scanner 1006. System 1000 may also include a storage controller 1007 for interfacing with one or more storage devices 1008 each of which includes a storage medium such as magnetic tape or disk, or an optical medium that might be used to record programs of instructions for operating systems, utilities and applications which may include embodiments of programs that implement various aspects of the present disclosure. Storage device(s) 1008 may also be used to store processed data or data to be processed in accordance with the disclosure. System 1000 may also include a display controller 1009 for providing an interface to a display device 1011, which may be a cathode ray tube (CRT), a thin film transistor (TFT) display, or other type of display. System 1000 may also include a printer controller 1012 for communicating with a printer 1013. A communications controller 1014 may interface with one or more communication devices 1015, which enables system 1000 to connect to remote devices through any of a variety of networks including the Internet, an Ethernet cloud, an FCoE/DCB cloud, a local area network (LAN), a wide area network (WAN), a storage area network (SAN) or through any suitable electromagnetic carrier signals including infrared signals.

In the illustrated system, all major system components may connect to a bus 1016, which may represent more than one physical bus. However, various system components may or may not be in physical proximity to one another. For example, input data and/or output data may be remotely transmitted from one physical location to another. In addition, programs that implement various aspects of this disclosure may be accessed from a remote location (e.g., a server) over a network. Such data and/or programs may be conveyed through any of a variety of machine-readable medium including, but are not limited to: magnetic media such as hard disks, floppy disks, and magnetic tape; optical media such as CD-ROMs and holographic devices; magneto-optical media; and hardware devices that are specially configured to store or to store and execute program code, such as application specific integrated circuits (ASICs), programmable logic devices (PLDs), flash memory devices, and ROM and RAM devices.

Embodiments of the present disclosure may be encoded upon one or more non-transitory computer-readable media with instructions for one or more processors or processing units to cause steps to be performed. It shall be noted that the one or more non-transitory computer-readable media shall include volatile and non-volatile memory. It shall be noted that alternative implementations are possible, including a hardware implementation or a software/hardware implementation. Hardware-implemented functions may be realized using ASIC(s), programmable arrays, digital signal processing circuitry, or the like. Accordingly, the "means" terms in any claims are intended to cover both software and hardware implementations. Similarly, the term "computer-readable medium or media" as used herein includes software and/or hardware having a program of instructions embodied thereon, or a combination thereof. With these implementation alternatives in mind, it is to be understood that the figures and accompanying description provide the functional information one skilled in the art would require to write program code (i.e., software) and/or to fabricate circuits (i.e., hardware) to perform the processing required.

It shall be noted that embodiments of the present disclosure may further relate to computer products with a non-transitory, tangible computer-readable medium that have computer code thereon for performing various computer-implemented operations. The media and computer code may be those specially designed and constructed for the purposes of the present disclosure, or they may be of the kind known or available to those having skill in the relevant arts. Examples of tangible computer-readable media include, but are not limited to: magnetic media such as hard disks, floppy disks, and magnetic tape; optical media such as CD-ROMs and holographic devices; magneto-optical media; and hardware devices that are specially configured to store or to store and execute program code, such as application specific integrated circuits (ASICs), programmable logic devices (PLDs), flash memory devices, and ROM and RAM devices. Examples of computer code include machine code, such as produced by a compiler, and files containing higher level code that are executed by a computer using an interpreter. Embodiments of the present disclosure may be implemented in whole or in part as machine-executable instructions that may be in program modules that are executed by a processing device. Examples of program modules include libraries, programs, routines, objects, components, and data structures. In distributed computing environments, program modules may be physically located in settings that are local, remote, or both.

One skilled in the art will recognize no computing system or programming language is critical to the practice of the present disclosure. One skilled in the art will also recognize that a number of the elements described above may be physically and/or functionally separated into sub-modules or combined together.

It will be appreciated to those skilled in the art that the preceding examples and embodiment are exemplary and not limiting to the scope of the present disclosure. It is intended that all permutations, enhancements, equivalents, combinations, and improvements thereto that are apparent to those skilled in the art upon a reading of the specification and a study of the drawings are included within the true spirit and scope of the present disclosure.

What is claimed is:

1. A system for accurately measuring gas temperature, the system comprising:
   a temperature logging device comprising an enclosure, the enclosure comprises a sensing element to measure a gas temperature, the temperature logging device performing the steps of:
   using a temperature probe located within a probe enclosure to determine a probe temperature;
   determining a first time constant associated with the temperature probe;
   determining a second time constant associated with the probe enclosure;

determining, based on the probe temperature, the first time constant, the second time constant, and an ambient temperature within a chamber that holds at least the temperature probe and the probe enclosure; and using at least one of the first and second time constants to obtain compensated data that is compensated for a time lag between the probe temperature and an actual temperature; and using the compensated data to determine the actual temperature; and a capsule that at least partially seals the temperature logging device and comprises at least one through hole that provides access to the temperature logging device.

2. The system according to claim 1, wherein the enclosure is removably attached to the capsule.

3. The system according to claim 1, wherein the enclosure comprises a top cover and a bottom cover.

4. The system according to claim 3, wherein the at least one of the top cover and bottom cover is electrically connected to the integrated circuit, the at least one of the top cover and bottom cover serving as an electrode.

5. The system according to claim 1, wherein the one or more processors comprise a power saving circuit comprising a sleep mode that is activated between two measurement cycles.

6. The system according to claim 1, further comprising a communication circuit coupled to the one or more processors, the communication circuit being coupled to a wireless communication device that communicates the temperature data to a reader.

7. The system according to claim 1, wherein the sensing element is a digital temperature sensor.

8. The system according to claim 1, wherein the integrated circuit is affixed to the enclosure via a thermal conductor.

9. The system according to claim 1, further comprising a digital filter that filters out noise from the temperature data.

10. A method for accurately measuring gas temperature, the method comprising:

using a temperature probe located within a probe enclosure to determine a probe temperature;

determining a first time constant associated with the temperature probe that;

determining a second time constant associated with the probe enclosure;

determining, based on the probe temperature, the first time constant, the second time constant, and an ambient temperature within a chamber that holds at least the temperature probe and the probe enclosure; and using at least one of the first and second time constants to obtain compensated data that is compensated for a thermal lag between the probe temperature and an actual temperature; and using the compensated data to determine the actual temperature.

11. The method according to claim 10, wherein determining at least one of the first and second time constants comprises using an equation $$T_A = Tp + (\tau_1 + \tau_2)\frac{dTp}{dt} + (\tau_1 \tau_2)\frac{d^2 Tp}{dt^2}$$

wherein $T_A$ is the actual temperature, $T_p$ is the probe temperature, $\tau_1$ $(=C_p/k_1)$ is a probe time constant, and $\tau_2$ $(=C_E/k_2)$ is a probe enclosure time constant.

12. The method according to claim 10, wherein at least one of the first and second time constants is at least partially experimentally determined.

13. The method according to claim 10, wherein determining at least one of the first and second time constants comprises adjusting at least one of the first and second time constants based on at least one of a location of the temperature probe within the chamber, the presence and nature of objects in the chamber, an initial temperature of the chamber, a type of a heating cycle, a time interval during which a target sterilization temperature is maintained, and an absolute value of the target sterilization temperature.

14. The method according to claim 10, further comprising determining the probe temperature based on a plurality of test cycles.

15. The method according to claim 10, further comprising filtering out noise from the ambient temperature data.

16. An IC-based temperature logging device for accurately measuring gas temperature, the temperature logging device performing the steps of:

determining a first time constant associated with a temperature probe located within a probe enclosure;

determining a second time constant associated with the probe enclosure;

using the temperature probe to measure an ambient temperature within a chamber that hold least the temperature probe and the probe enclosure; and using at least one of the first and second time constants obtain compensated data that is compensated for a thermal lag between the ambient temperature and an actual temperature; and using the compensated data to determine the actual temperature.

17. The temperature logging device according to claim 16, wherein the integrated circuit comprises memory to store temperature data.

18. The temperature logging device according to claim 16, wherein the temperature probe is removably attached to the enclosure.

19. The temperature logging device according to claim 16, wherein the probe enclosure is hermetically sealed and comprises a top and bottom cover.

20. The temperature logging device according to claim 19, wherein the top and bottom cover serve as electrodes.

* * * * *